(12) United States Patent
DeLeo et al.

(10) Patent No.: US 6,514,493 B1
(45) Date of Patent: Feb. 4, 2003

(54) CDNA CLONE FOR TUMOR REJECTION ANTIGEN GP110 AND TUMOR PEPTIDE VACCINE

(75) Inventors: Albert B. DeLeo, Pittsburgh, PA (US); Douglas Loftus, Silver Spring, MD (US); Ettore Appella, Chevy Chase, MD (US)

(73) Assignee: University of Pittsburgh of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 08/897,843

(22) Filed: Jul. 21, 1997

(51) Int. Cl.$^7$ .......................... A61K 35/12; A61K 48/00; C07H 21/04
(52) U.S. Cl. .................. 424/93.1; 424/93.7; 424/93.71; 514/44; 536/23.1; 536/23.5
(58) Field of Search .............................. 536/23.1, 23.5; 514/44; 424/93.1, 93.7, 93.71

(56) References Cited

PUBLICATIONS

Dayoff et al, Atlas of Protein Sequence and Structure, vol. 5, suppl. 3, pp. 345–362, M.O. Dayoff, Ed., National Biomedical Research foundation, Washington, D.C., 1979.*

Burgess et al "Possible Dissociation of the Heparin–binding and Mitogenic Acitivies of Heparin–binding Growth Factor–1 from Its Receptor–binding Activities by Site–directed Mutagenesis of a single Lysine Residue", Journal of Cellular biology, vol. 111, pp, 1990.*

Lazar et al, "Transforming Growth Factor Alpha: Mutation of Aspartic Acid 47 and Leuine 48 Results in Different Biological Activities", Molecular and Cellular Biology, vol. 8, pp. 1247–1252, 1988.*

Davis et al, "Direct gene transfer into skeletal muscle", Human Gene therapy, vol. 4, pp. 151–159, Mar. 1993.*

Crystal, R.G., "In vivo and ex vivo gene therapy strategies to treat tumors using adenovirus gene transfer vectors", Cancer chemotherapeutics and pharmacology, vol. 43, suppl., S90–S99, 1999.*

Genebank Accession No.: Q 14697 (Nov. 1, 1996).*
Genebank Accession No.: P 79403 (May 1, 1997).*
Genebank Accession No.: AA 239684 (Mar. 12, '97).*
Genebank Accession No.: U71273 (Mar. 18, 1997).*

De Leo et al., "Properties of a $M_r$ 110,000 Tumor Rejection Antigen of the Chemically Induced BALB/c Meth A Sarcoma", Cancer Research, vol. 53, pp. 1602–1607, (Apr. 1, 1993).

Fassanito et al., "Characterization of Cloned I MHC–restricted, CD8$^+$ Anti–Meth A Cytotoxic T–Lymphocytes: Recognition of an Epitope Derived from the Meth A gp110 Tumor Rejection Antigen", Cancer Research, vol. 54, pp. 4424–4429 (Aug. 15, 1994).

Mayordomo et al., "Bone marrow–derived dendritic cells pulsed with synthetic tumour peptides elicit protective and therapeutic antitumour immunity", Nature Medicine, vol. 1, No. 12, pp. 1297–1302 (Dec. 1995).

Mayordomo et al., "Therapy of Murine Tumors with p53 Wild–type and Mutant Sequence Peptide–based Vaccines", J. Exp. Med., vol. 183, pp. 1357–1365 (Apr. 1996).

Arendt et al., "Identification of the CD45–associated 116–kDa and 80–kDa Proteins as the α– and β–Subunits of α–Glucosidase II", The Journal of Biological Chemistry, May 16, 1997, pp. 13117–13125, vol. 272, No. 20, USA.

* cited by examiner

Primary Examiner—Anthony C. Caputa
Assistant Examiner—Karen A. Canella
(74) Attorney, Agent, or Firm—Debra Z. Anderson; Eckert Seamans Cherin & Mellott, LLC

(57) ABSTRACT

An isolated cDNA molecule comprising an amino acid sequence encoding an amino-terminal protein fragment of murine glycoprotein 110 is disclosed. Therapeutic methods for treating tumor-bearing patients are also disclosed, as are prophylactic methods for vaccinating patients. An animal model for studying tumors is also disclosed.

7 Claims, 14 Drawing Sheets

SEQUENCE LISTING (1) GENERAL INFORMATION:

(i) APPLICANT: DeLeo, Albert B.; Loftus, Douglas; Appella, Ettore (ii) TITLE OF INVENTION: CDNA CLONE FOR MURINE TUMOR
       REJECTION ANTIGEN GP110 AND TUMOR PEPTIDE VACCINE (iii) NUMBER OF SEQUENCES: 12

(iv) CORRESPONDENCE ADDRESS:
       (A) ADDRESSEE: Diane R. Meyers
       (B) STREET: 600 Grant Street, 42nd Floor
       (C) CITY: Pittsburgh
       (D) STATE: PA
       (E) COUNTRY: USA
       (F) ZIP: 15219

(v) COMPUTER READABLE FORM:
       (A) MEDIUM TYPE: Floppy disk
       (B) COMPUTER: IBM PC compatible
       (C) OPERATING SYSTEM: PC-DOS/MS-DOS
       (D) SOFTWARE: PatentIn Release #1.0, Version #1.25

(vi) CURRENT APPLICATION DATA:
       (A) APPLICATION NUMBER:
       (B) FILING DATE:
       (C) CLASSIFICATION:

(2) INFORMATION FOR SEQ ID NO:1:

(i) SEQUENCE CHARACTERISTICS:
       (A) LENGTH: 938 amino acids
       (B) TYPE: amino acid
       (D) TOPOLOGY: linear (ii) MOLECULE TYPE:

(iii) HYPOTHETICAL: NO (iv) ANTI-SENSE: NO (v) FRAGMENT TYPE: N-terminal (vi) ORIGINAL SOURCE:
       (A) ORGANISM: Mus musculus
       (D) DEVELOPMENTAL STAGE: Embryo
       (F) TISSUE TYPE: Embryo
       (H) CELL LINE: NIH 3T3

Figure 1A

(xi) SEQUENCE DESCRIPTION: SEQ ID NO:1:

```
Ala Ala Val Ala Ala Arg Arg Arg Arg Ser Trp Leu Ser Leu Val Leu
 1               5                  10                  15

Ala Tyr Leu Gly Val Cys Leu Gly Ile Thr Leu Ala Val Asp Arg Ser
                20                  25                  30

Asn Phe Lys Thr Cys Asp Glu Ser Ser Phe Cys Lys Arg Gln Arg Thr
            35                  40                  45

Ile Arg Pro Gly Leu Ser Pro Tyr Pro Ser Leu Leu Asp Thr Leu Gln
    50                  55                  60

Leu Gly Pro Asp Ala Leu Thr Val His Leu Ile His Glu Val Thr Lys
65                  70                  75                  80

Val Leu Leu Val Leu Glu Leu Gln Gly Leu Gln Lys Asn Met Thr Arg
                85                  90                  95

Ile Arg Ile Asp Glu Leu Glu Pro Arg Pro Arg Tyr Arg Val Pro Asp
            100                 105                 110

Val Leu Val Ala Asp Pro Pro Thr Ala Arg Leu Ser Val Ser Gly Arg
            115                 120                 125

Asp Asp Asn Ser Val Glu Leu Thr Val Ala Glu Gly Pro Tyr Lys Ile
    130                 135                 140

Ile Leu Thr Ala Gln Pro Phe Arg Leu Asp Leu Leu Glu Asp Arg Ser
145                 150                 155                 160

Leu Leu Leu Ser Val Asn Ala Arg Gly Leu Met Ala Phe Glu His Gln
                165                 170                 175

Arg Ala Pro Arg Val Pro Gln Glu Ser Lys Asp Pro Ala Glu Gly Asn
            180                 185                 190

Gly Ala Gln Pro Glu Ala Thr Pro Gly Asp Gly Asp Lys Pro Glu Glu
            195                 200                 205

Thr Gln Glu Lys Ala Glu Lys Asp Glu Pro Gly Ala Trp Glu Glu Thr
    210                 215                 220

Phe Lys Thr His Ser Asp Ser Lys Pro Tyr Gly Pro Thr Ser Val Gly
225                 230                 235                 240

Leu Asp Phe Ser Leu Pro Gly Met Glu His Val Tyr Gly Ile Pro Glu
                245                 250                 255

His Ala Asp Ser Leu Arg Leu Lys Val Thr Glu Gly Gly Glu Pro Tyr
            260                 265                 270

Arg Leu Tyr Asn Leu Asp Val Phe Gln Tyr Glu Leu Asn Asn Pro Met
    275                 280                 285

Ala Leu Tyr Gly Ser Val Pro Val Leu Leu Ala His Ser Phe His Arg
    290                 295                 300
```

Figure 1B

```
Asp Leu Gly Ile Phe Trp Leu Asn Ala Ala Glu Thr Trp Val Asp Ile
             310                 315                 320

Ser Ser Asn Thr Ala Gly Lys Thr Leu Phe Gly Lys Met Leu Asp Tyr
             325                 330                 335

Leu Gln Gly Ser Gly Glu Thr Pro Gln Thr Asp Ile Arg Trp Met Ser
             340                 345                 350

Glu Ser Gly Ile Ile Asp Val Phe Leu Met Leu Gly Pro Ser Val Phe
             355                 360                 365

Asp Val Phe Arg Gln Tyr Ala Ser Leu Thr Gly Thr Gln Ala Leu Pro
             370                 375                 380

Pro Leu Phe Ser Leu Gly Tyr His Gln Ser Arg Trp Asn Tyr Arg Asp
385                  390                 395                 400

Glu Ala Asp Val Leu Glu Val Asp Gln Gly Phe Asp Asp His Asn Met
                 405                 410                 415

Pro Cys Asp Val Ile Trp Leu Asp Ile Glu His Ala Asp Gly Lys Arg
             420                 425                 430

Tyr Phe Thr Trp Thr Pro Thr Arg Phe Pro Gln Pro Leu Asn Met Leu
         435                 440                 445

Glu His Leu Asp Ser Lys Arg Arg Asn Val Val Ala Ile Val Asp Pro
450                  455                 460

His Ile Lys Val Asp Ser Gly Tyr Arg Val His Glu Glu Leu Arg Asn
465                  470                 475                 480

His Gly Leu Tyr Val Lys Thr Arg Asp Gly Ser Asp Tyr Glu Gly Trp
                 485                 490                 495

Cys Trp Pro Gly Ser Ala Ser Tyr Pro Asp Phe Thr Asn Pro Arg Met
             500                 505                 510

Arg Ala Leu Trp Ser Asn Met Phe Ser Phe Asp Asn Tyr Glu Gly Ser
             515                 520                 525

Ala Pro Asn Leu Tyr Val Trp Asn Asp Met Asn Glu Pro Ser Val Phe
             530                 535                 540

Asn Gly Pro Glu Val Thr Met Leu Lys Asp Ala Val His Tyr Gly Gly
545                  550                 555                 560

Trp Glu His Arg Asp Ile His Asn Ile Tyr Gly Leu Tyr Val His Met
                 565                 570                 575

Ala Thr Ala Asp Gly Leu Ile Gln Arg Ser Gly Gly Ile Glu Arg Pro
             580                 585                 590

Phe Val Leu Ser Arg Ala Phe Phe Ser Gly Ser Gln Arg Phe Gly Ala
             595                 600                 605

Val Trp Thr Gly Asp Asn Thr Ala Glu Trp Asp His Leu Lys Ile Ser
         610                 615                 620
```

Figure 1C

```
Ile Pro Met Cys Leu Ser Leu Ala Leu Val Gly Leu Ser Phe Cys Gly
625                 630                 635                 640

Ala Asp Val Gly Gly Phe Phe Lys Asn Pro Glu Pro Glu Leu Leu Val
                645             650                 655

Arg Trp Tyr Gln Met Gly Ala Tyr Gly Pro Phe Phe Arg Ala His Ala
            660             665                 670

Thr Trp Thr Leu Gly Gly Glu Ser Met Ala Val Ser Val Ser Ile Pro
        675                 680                 685

Arg Cys Asn Pro Arg Cys Leu Val Pro Ala Ile Phe Phe Ala Ala Leu
    690             695                 700

Leu Val Tyr Pro Leu Leu Ser Ser Ser Gln Gly Arg Val Ser Cys His
705                 710                 715                 720

Glu Ala Pro Leu Val Gln Tyr Pro Glu Asp Met Ser Thr Phe Ser Ile
                725             730                 735

Glu Asp Gln Phe Met Leu Gly Asp Ala Leu Leu Ile His Pro Val Ser
            740             745                 750

Asp Ala Gly Ala His Gly Gly Arg Ser Ile Cys Leu Ala Lys Lys Arg
        755             760                 765

Cys Gly Met Thr Phe Arg Ala Ile Arg Ser Ile Met Gly Pro Arg Pro
    770             775                 780

Cys Ile Cys Pro Val Thr Leu Ser Ser Ile Pro Val Phe Gln Gly Gly
785             790                 795                 800

Gly Thr Ile Val Pro Arg Trp Met Arg Val Arg Arg Ser Ser Asp Cys
                805             810                 815

Met Lys Asp Asp Pro Ile Thr Leu Phe Val Ala Leu Ser Pro Gln Gly
            820             825                 830

Thr Ala Gln Gly Glu Leu Phe Leu Asp Asp Gly His Thr Phe Asn Tyr
        835             840                 845

Gln Thr Arg His Glu Phe Leu Leu Arg Arg Phe Ser Phe Ser Gly Ser
    850             855                 860

Thr Leu Val Ser Ser Ala Asp Pro Lys Gly His Leu Glu Thr Pro
865             870             875                 880

Ile Trp Ile Glu Arg Val Val Ile Met Gly Ala Gly Lys Pro Ala Ala
                885             890                 895

Val Val Leu Gln Thr Lys Gly Ser Pro Glu Ser Arg Leu Ser Phe Gln
            900             905                 910

His Asp Pro Glu Thr Ser Val Leu Ile Leu Arg Lys Pro Gly Val Ser
        915             920                 925

Val Ala Ser Asp Trp Ser Ile His Leu Arg
        930             935
```

Figure 1D (3) INFORMATION FOR SEQ ID NO:2:

(i) SEQUENCE CHARACTERISTICS:
        (A) LENGTH: 50
        (B) TYPE: amino acid
        (C) TOPOLOGY: linear (ii) MOLECULE TYPE:

```
Pro Lys Glu Leu Val Leu Ser Trp Glu Glu Gly His Asp Gly Ile Glu
1               5                   10                  15

Leu Pro Phe Leu Leu Pro Trp Ser Leu Thr Leu Pro Arg Phe His Leu
            20                  25                  30

Leu Ile Leu Arg Pro Arg Phe Cys Gln His Leu Gly Lys Met Thr Gly
        35                  40                  45

Leu Ser
    50
```

Figure 1E (4) INFORMATION FOR SEQ ID NO:3:

(i) SEQUENCE CHARACTERISTICS:
      (A) LENGTH: 6
      (B) TYPE: amino acid
      (C) TOPOLOGY: linear (ii) MOLECULE TYPE:

```
Gly Ser Glu Phe His Leu
1               5
```

(5) INFORMATION FOR SEQ ID NO:4:

(i) SEQUENCE CHARACTERISTICS:
      (A) LENGTH: 63
      (B) TYPE: amino acid
      (C) TOPOLOGY: linear (ii) MOLECULE TYPE:

```
Pro Ser Leu Ser Phe Cys Val Leu Pro Ser Pro Ser Tyr Ser Val Ser
1               5                   10                  15

Cys Cys Cys Asn Trp Ser Thr Val Ile Cys Glu His Gln Gly Ala Leu
            20                  25                  30

Ser Phe Phe Phe Ser Ser Leu Gly Ser Leu Pro Ser Pro Tyr Thr Pro
        35                  40                  45

Ser Ile Gln Ala Ser Cys Leu Leu Met Pro Phe Leu Gly Arg Arg
    50                  55                  60
```

(6) INFORMATION FOR SEQ ID NO:5

(i) SEQUENCE CHARACTERISTICS:
      (A) LENGTH: 23
      (B) TYPE: amino acid
      (C) TOPOLOGY: linear (ii) MOLECULE TYPE:

```
Thr Leu Gly Phe Leu Phe Phe Phe Pro Val Pro Ser Tyr Pro Lys Cys
1               5                   10                  15

Pro Ser Phe His Ser Phe Pro
                20
```

Figure 1F (7) INFORMATION FOR SEQ ID NO:6

(i) SEQUENCE CHARACTERISTICS:
        (A) LENGTH: 7
        (B) TYPE: amino acid
        (C) TOPOLOGY: linear (ii) MOLECULE TYPE:

Met Ser Pro Ser Leu Phe His
1               5

(8) INFORMATION FOR SEQ ID NO:7

(i) SEQUENCE CHARACTERISTICS:
        (A) LENGTH: 44
        (B) TYPE: amino acid
        (C) TOPOLOGY: linear (ii) MOLECULE TYPE:

Tyr Thr Gly Thr Thr Pro Tyr Leu Val Arg Asp Lys Trp Ile Lys Ile
1               5                   10                  15
Glu Val Pro Gly Glu Arg Pro Leu Pro Ser His Leu Asn Leu Val Phe
            20                  25                  30
Leu Phe Leu Ser Arg Ala Ala Ala Phe Leu Pro Ser
            35                  40

(9) INFORMATION FOR SEQ ID NO:8

(i) SEQUENCE CHARACTERISTICS:
        (A) LENGTH: 7
        (B) TYPE: amino acid
        (C) TOPOLOGY: linear (ii) MOLECULE TYPE:

Arg Glu Thr Leu Pro His Asn
1               5

Figure 1G

(10) INFORMATION FOR SEQ ID NO:9

(i) SEQUENCE CHARACTERISTICS:
        (A) LENGTH: 57
        (B) TYPE: amino acid
        (C) TOPOLOGY: linear (ii) MOLECULE TYPE:

```
Glu Gly Lys Val Ile Lys Leu Leu Leu Pro Leu Trp Ser Pro Trp Asp
 1               5                  10                  15

Thr Gln Asp Arg Asp Met Ser Cys Gly Phe Thr Glu Ser Arg Ser Pro
             20                  25                  30

Val Phe Ile Ala Gly Lys Lys Thr Glu Gly Gly Gly Arg Arg Ser Cys
         35                  40                  45

Val Pro Arg Gly Gly Phe Lys Pro Trp
     50                  55
```

(11) INFORMATION FOR SEQ ID NO:10

(i) SEQUENCE CHARACTERISTICS:
        (A) LENGTH: 32
        (B) TYPE: amino acid
        (C) TOPOLOGY: linear (ii) MOLECULE TYPE:

```
Gly Arg Thr Gln Glu Pro Gly Glu Leu Phe Val Gly Ile Phe Phe Thr
 1               5                  10                  15

Ser Ser Gly Phe Pro Thr Val Thr Ser Phe Asp Lys Lys Glu Lys Gln
             20                  25                  30
```

(12) INFORMATION FOR SEQ ID NO:11

(i) SEQUENCE CHARACTERISTICS:
        (A) LENGTH: 16
        (B) TYPE: amino acid
        (C) TOPOLOGY: linear (ii) MOLECULE TYPE:

```
Lys Thr Lys Gln Asn Ile Asn Asn Asn Trp Met Ser Glu Leu Tyr Leu
 1               5                  10                  15
```

Figure 1H

(13) INFORMATION FOR SEQ ID NO:12

(i) SEQUENCE CHARACTERISTICS:
  (A) LENGTH: 8
  (B) TYPE: amino acid
  (C) TOPOLOGY: linear (ii) MOLECULE TYPE:

Thr Glu Gln Asn Arg Ser Ser Lys
1       5

Figure 1I

| | | | | | |
|---|---|---|---|---|---|
| CMS4-1 | LAVDRSNFK  | EESSFCKRQ | RSIRPGLSPY | RALLDSLQLG | PDSL VHLIH |
| alpha-1 | LAVDRSNFK | EESSFCKRQ | RSIRPGLSPY | RALLDSLQLG | PDSL VRLIH |
| alpha-2 | LAVDRSNFK | EESSFCKRQ | RSIRPGLSPY | RALLDSLQLG | PDSL VHLIH |
| alpha-3 | LAVDRSNFK | EESSFCKRQ | RSIRPGLSPY | RALLDSLQLG | PDSL VHLIH |
| beta-1 | LAVDRSNFK | DESSFCKRQ | R IRPGLSPY | RALLD LQLG | PDAL VHLIH |
| beta-2 | LAVDRSNFK | DESSFCKRQ | RSIRPGLSPY | RALLD LQLG | PDAL VHLIH |
| Meth A-1 | NFK | DESSFCKRQ | R IRPGLSPY | RALLD LQLG | PDAL VHLIH |
| CMS4-2 | | KRQ | R IRPGLSPY | RALLD LQLG | PDAL VHLIH |

| | | | | | |
|---|---|---|---|---|---|
| CMS4-1 | EV KVLLVLE | LQGLRKNMAR | FRIDELEPRR | PRYRVPDVLV | ADPPMARLSV |
| alpha-1 | EV KVLLVLE | LQGLRKNM R | FRIDELEPRR | PRYRVPDVLA | ADPPMARLSV |
| alpha-2 | EV KVLLVLE | LQGLQKNM R | FRIDELEPRR | PRYRVPDVLV | ADPPMARLSV |
| alpha-3 | EV KVLLVLE | LQGPRKNM R | FRIDELEPRR | PRYRVPDVLV | ADPPMARLSV |
| beta-1 | EV KVLLVLE | LQGLQKNM R | IRIDELEP R | LRYRVPDVLV | ADPP ARLSV |
| beta-2 | EV KVLLVLE | LQGLQKNM R | IRIDELEPRR | PRYRVPDVLV | ADPP ARLSV |
| Meth A-1 | EV KVLLVLE | LQGLQKNM R | IRIDELEPRx | PRYRVPDVLV | ADPP ARLSV |
| CMS4-2 | EV KVLLVLE | LQGLQKNM R | IRIDELES RR | LRYRVP | |

| | | | | | |
|---|---|---|---|---|---|
| CMS4-1 | SGRDENSVEL | MAEEPYKII | L ARPFRLDL | LEDRSLLLSV | NARGLLEFEH |
| alpha-1 | SGRDENSVEL | MAEEPYKII | L ARPFRLDL | LEDRSLLLSV | NARGLLEFEH |
| alpha-2 | SGRDENSVEL | MAEEPYKII | L ARPFRLDL | LEDRSLLLSV | NARGLLEFEH |
| alpha-3 | SGRDENSVEL | MAEEPYKII | L ARPFRLDL | LEDRSLLLSV | NARGLLEFEH |
| beta-1 | SGRDDNSVEL | VAEGPYKII | L AQPFRLDL | LEDRSLLLSV | NARGLMAFEH |
| beta-2 | SGRDDNSVEL | VAEGPYKII | L AQPFRLDL | LEDRSLLLSV | NARGLMAFEH |
| Meth A-1 | SGRDENSVEL | VAEGPYKII | L AQPFRLDL | LEDRSLLLSV | NARGLMAFEH |

| | | | | |
|---|---|---|---|---|
| CMS4-1 | QRAPRVSQGS | KDPAEGDGAQ | PEE PRDGDK | PEE |
| alpha-1 | QRAPRVSQGS | KDPAEGDGAQ | PEE PRDGDK | PEE |
| alpha-2 | QKAPRVSQGS | KDPAEGDGAQ | PEE PRDGDK | PEE |
| alpha-3 | QRAPRVSQGS | KDPAEGDGAQ | PEE PRDGDK | PEE |
| beta-1 | QRAPRVPQES | KDPAEGNGAQ | PEA PGDGDK | PEE |
| beta-2 | QRAPRVPQES | KDPAEGNGAQ | PEA PGDGDK | PEE |
| Meth A-1 | QRAPRVPQES | KDPAEGNGAQ | PEA PGDGDK | PEE |

Figure 6

CDNA CLONE FOR TUMOR REJECTION ANTIGEN GP110 AND TUMOR PEPTIDE VACCINE

This work was supported, in part, by National Institute of Health grant CA42276.

BACKGROUND OF THE INVENTION

1. Field of the Invention

The present invention is directed to the amino acid sequence for cDNA encoding the tumor rejection antigen known as gp 110. More specifically, the present invention provides an amino acid sequence for murine gp110, including identification of the amino-terminal sequence as defined by automated Edman degradation sequencing. Prophylactic and therapeutic methods for using gp110 are also disclosed.

2. Background Information

T-cell mediated responses play an important role in a host's immune response to viral infections and cancer. T-cells function by recognizing an antigen in the context of relatively short peptides. These antigenic peptides, which have been processed from exogenous and endogenous proteins, are presented on the cell's surface in association with Class I and II MHC molecules. As a result, any cell can literally display on its cell surface an array of peptides, derived from proteins found within the cell, for continuous sampling and evaluation by various T-cell populations. For example, $CD8^+$ cytolytic T-cells (CTL) recognize a non-covalent trimeric complex of a given MHC Class I heavy chain allele, $\beta_2$-m, and a peptide comprised of 8 to 12 amino acid residues. Such complexes may be amino affinity purified, denatured in vitro, and the peptides isolated and sequenced. These peptides can then be used in the formation of peptide-based vaccines.

The concept of immunity against tumors is based on the fact that tumor cells carry antigens that are not detect on normal cells. Two classes of tumor antigens have been identified: tumor specific antigens (TSA) and tumor associated antigens. Tumor specific antigens are unique to tumor cells and do not occur on other cells in the body. Tumor-associated antigens are not unique to the tumor cells and instead are also expressed on normal cells under conditions that fail to induce a state of immunologic tolerance to the antigen. The expression of the antigen on the tumor may occur under conditions that enable the immune system to respond to the antigen. Tumor-associated antigens may be antigens that are expressed on normal cells during fetal development when the immune system is immature and unable to respond or they may be antigens that are normally present at extremely low levels on normal cells, but which are expressed at much higher levels on tumor cells.

In general, tumor antigens are defined by their ability to elicit a humoral and/or cell-mediated response. Although a few tumor antigens have been shown to induce the production of humoral antibodies, most induce a cell-mediated response. A class of tumor antigens has been shown to elicit cell-mediated responses in mice that result in rejection of tumors, expressing these antigens when they are transplanted into syngeneic recipients. Because of this phenomenon, these tumor antigens are referred to as tumor specific transplantation antigens (TSTA), tumor rejection antigens (TRA), or tumor-associated transplantation antigens (TATAs).

Studies of the immunogenicity of chemically induced sarcomas of inbred mice established the concept of TSA and revealed their potential role in cancer immunotherapy. Three murine TRA have been isolated from the chemically induced BALB/c Meth A sarcoma and other tumors and are believed to have restricted tumor rejection inducing activities. These three TRA are known as $M_r$ 82,000 (p82), $M_r$ 84,000/86,000 (HSP84/86) and $M_r$ 96,000 (gp96). The HSP84/86 and gp96 TRA are stress-induced proteins; the HSP84/86 antigens are the murine equivalents of the $M_r$ 90,000 heat-shock proteins, while gp96 is identical to the glucose-regulated protein GRp94.

A Meth A TRA identified as $M_r$ 110,000 (gp110) appears to be antigenically distinct from previously identified TRA isolated from Meth A, and responsible for the highly restricted tumor rejection-inducing activity of this tumor. The gp110 family of tumor antigens is a novel set of tumor rejection antigens that appear to be responsible for the antigenic diversity of chemically-induced sarcomas and other tumor types known to express antigenically diverse TRAs as well. Based on their well-characterized functional activity as tumor rejection antigens, the translational potential of gp110 in the development of clinical peptide-based vaccines is significant.

DeLeo, et al. "Properties of a $M_r$ 110,000 Tumor Rejection Antigen of the Chemically Induced BALB/c Meth A Sarcoma", *Cancer Res.* 53:1602–1607 (1993) reported that it appears to be gp110, and not gp96, that has tumor rejection inducing activity.

Fassanito, et al. "Characterization of Cloned Class I MHC-restricted, $CD8^+$ Anti-Meth A Cytotoxic T-Lymphocytes: Recognition of an Epitope Derived from the Meth A gp110 Tumor Rejection Antigen", *Cancer Res.* 55:124–128 (1995) reported that the determinant recognized by the cloned anti-Meth A CTL line (CTLMA-ac) is derived from Meth A gp110.

Mayordomo, et al. "Bone Marrow-derived Dendritic Cells Pulsed with Synthetic Tumor Peptides Elicit Protective and Therapeutic Antitumor Immunity", *Nature Medicine* 1:1297–1302 (1995) discuss the use of tumor peptide-pulsed dendritic cells.

Mayordomo, et al. "Therapy of Murine Tumors with p53 Wild-type and Mutant Sequence Peptide-based Vaccines", *J. Exp. Med.*, 183:1357–1365 (1996) discuss the immunization of mice with bone-marrow derived dendritic cells prepulsed with Meth A p53 mutant peptide.

None of these articles provided the sequence of the gp110 molecule, disclosed the use of gp110 in CTL-defined peptide vaccines for the prophylactic treatment of a patient, or disclosed the use of a protein fragment, or cDNA encoding a protein fragment, comprising an amino terminal portion of gp110 for the therapeutic treatment of a patient.

SUMMARY OF THE INVENTION

The present invention is directed to the gp110 cDNA, defined as a cDNA encoding an amino acid sequence for murine gp110 molecule. This cDNA encodes a polypeptide, isolated by chromatography methods from Meth A sarcoma, comprising the N-terminal peptide of gp110 as determined by Edman sequencing, but does not include the initiator start codon for methionine. This cDNA clone also comprises the 3' untranslated region of gp110. More specifically, the present invention provides the amino acid sequence of this gp110 protein fragment. Methods for using gp110 based immunotherapy in both prophylactic and therapeutic settings are also disclosed.

It is therefore an object of the present invention to provide the amino acid sequence for the gp110 cDNA encoding the murine gp110 molecule.

A further object of the present invention is to provide prophylactic resistance to tumors in a patient.

Another object of this invention is to provide peptide-based and DNA based vaccines that induce anti-peptide CTL.

A further object of the invention is to provide therapeutic relief to patients with cancers expressing gp110 and variants of it.

These and other objects of the invention will be apparent from the following disclosure and claims.

BRIEF DESCRIPTION OF THE DRAWINGS

FIG. 1 shows the cloned murine glycoprotein 110 cDNA sequence of amino acid 1 to amino acid 1272 which depict SEQ ID NOS. 1–12, and identifies the fractions determined according to the methods of Example 8.

FIG. 4A shows the blot of Meth A (lanes 1, 3, 5) and BT-20 (lanes 2, 4, 6) with α-gp110 and mAb (lanes 5, 6) and control mAb (lanes 3, 4), and stained proteins (lanes 1, 2). FIG. 4B shows the blot of BT-20 with patients sera (lanes 1–4) and stained proteins (lane 5). FIG. 4C shows the blot of BT-20 (lanes 1, 2) and Meth A (lanes 2, 4) with a patient's serum (lanes 3, 4) and stained proteins (lanes 1, 2).

FIG. 6 shows the polymorphic character of gp110, which corresponds to codons 27–208 of SEQ ID NO: 1 as determined according to the methods of Example 6.

DETAILED DESCRIPTION OF THE INVENTION

Figure 2:
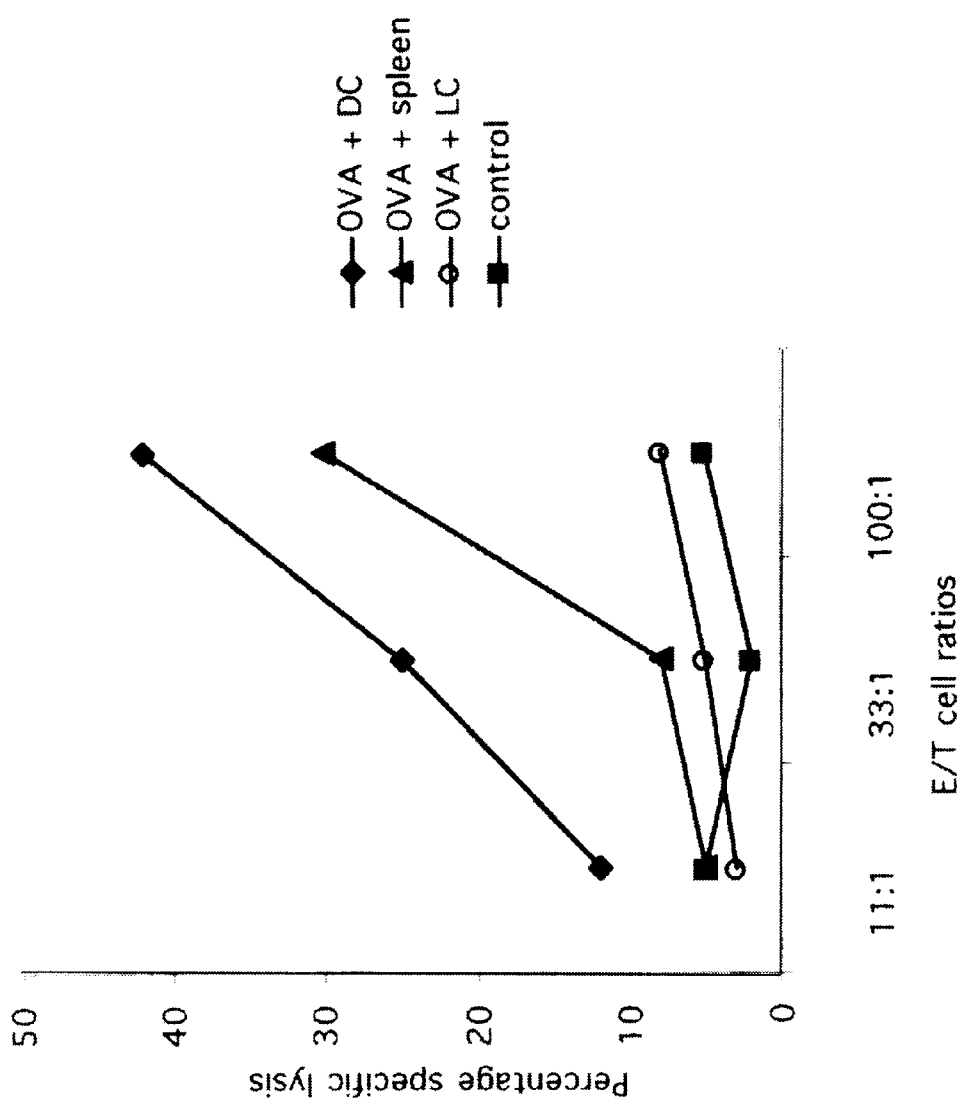
FIG. 2 shows a plot of E/T cell ratios versus perentage specific lysis, representing the induction of anti-OVA CTL using DC/OVA peptide determined according to the methods of Example 3.

The present invention is generally directed to the amino acid sequence of the gp110 murine tumor rejection antigen. More specifically, the present invention is directed to an isolated DNA molecule encoding a 938 aminated residue protein fragment of the murine glycoprotein 110. This isolated DNA molecule generally comprises amino acid 1 to amino acid 938 of the amino-terminal portion of the protein fragment, and conservatively modified variants thereof. The amino acid sequence of this peptide fragment is set forth in SEQ ID NO. 1.

As will be appreciated by those skilled in the art, an amino acid sequence can contain some variations in amino acids, while the overall sequence still codes for the same peptide or protein. For example, minor modifications to the amino acids in SEQ ID NOS. 1–12, such as variations in the amino acids, additional amino acids or fewer amino acids, can result in a protein with novel antigenic determinants, as well as the same physiological functions of gp110. As used herein the term "conservatively modified variants" and "conservatively altered sequences" refers to such variants of SEQ ID NOS. 1–12 which have the same physiological functions of gp110. Conservatively modified variants of SEQ ID NO. 1 can be tested for efficacy as gp110 by in vitro and/or in vivo based immunogenicity assays, and by using methods such as those taught in the examples below. Such assays and their methods of use will be well known to those skilled in the art. The gp110 sequence has been determined to be polymorphic, as is demonstrated in Example 8. The scope of the present invention, therefore, also encompasses polymorphic variations in SEQ ID NOS. 1–12, and homologous gp110 sequences found in other mammals.

FIG. 1 illustrates the amino acid code for the entire peptide isolated and reflects amino acids 1 through 1272. Amino acids 1 through 938 are further identified as SEQ ID NO. 1 and amino acids 940 through 1272 are included in SEQ ID NOS. 2–12. Stop codons are represented in the figure as "*" and are found at amino acid number 939, 990, 997, 1061, 1064, 1088, 1096, 1141, 1149, 1207, 1210, 1243, 1260, and 1269.

Sequencing was determined on a cDNA clone obtained from an raf-transformed NIH 3T3 cell. First, the amino acid sequence of the amino terminal peptide of Meth A gp110, isolated from Meth A sarcoma by chromatography methods, was determined by automated Edman degradation sequencing. The amino acid sequence for the amino terminal peptide, which generally corresponds with codons 29–46 of SEQ ID NO: 1 is: Val Asp Arg Ser Asn Phe Lys Thr His Asp Glu Ser Ser Phe Cys Lys Arg Gln. Then, a cDNA was cloned based in part on knowledge of this sequence. The cDNA was sequenced and translated. The amino terminal residue as determined by Edman sequencing, ran from amino acid residue 29 to amino acid residue 46.

The 5' end of the cDNA containing the methionine start codon was not isolated. Because the approximate size of gp110 mRNA, as detected in a Northern blot, is about 4,000 bases, and a sequence having about 3822 bases, has been identified, it is expected that the missing 5' end of the cDNA codes for an approximately 40–60 amino acid residue sequence.

Sequence analysis of the N-terminus and internal peptides of murine Meth A gp110 established that gp110 is a homogenous protein; no evidence of sequence heterogeneity was detected in several independently isolated preparations of gp110. The Meth A gp110 appears to be structurally unrelated to any presently known murine cellular or viral protein. In addition, delete sequence analysis of reverse transcriptase/polymerase chain reaction (RT/PCR) products derived from gp110 transcripts expressed in Meth A and CMS4 sarcomas has detected three apparent missense mutations in gp110.

The present invention is further directed to a substantially pure polypeptide fragment comprising gp110, which has tumor rejection inducing activity. One skilled in the art will appreciate that the term "tumor rejection inducing activity" refers to the activity of a polypeptide, protein, or fragments thereof, to induce tumor rejection. Preferably, the polypeptide fragment comprises amino acid 1 to amino acid 938. It may also comprise conservatively modified variants thereof. The present invention is further directed to vaccines utilizing peptides derived from this substantially pure polypeptide fragment or vaccines utilizing gp110 cDNA encoding these fragments.

In another embodiment of the present invention, a method for providing prophylactic resistance to tumors expressing T-cell-defined gp110 epitopes is provided. This method generally comprises vaccinating the host with an effective amount of a formulation comprising a polypeptide fragment comprising the portion of the glycoprotein 110 which has tumor rejection inducing ability. Preferably, this method employs a polypeptide fragment ranging from amino acid 1 to amino acid 938 and conservatively modified variants thereof.

This prophylactic method is preferably carried out by the use of antigen presenting cells (APC). As will be appreciated by those skilled in the art, APC are specialized cells that can provide the antigen-MHC ligand and the accessory signals required in the induction phase of CTL mediated immunity. General properties of APCs include MHC Class I and Class II expression, expression of various adhesion molecules important for APC-lymphocyte interaction, and expression of co-stimulatory molecules such as CD80 and CD86. Examples of APCs include macrophages and dendritic cells, such as cutaneous epidermal Langerhans cells, dermal dendritic cells, and dendritic cells resident in lymph nodes, the spleen and human peripheral blood. Dendritic cells are preferred in the methods of the present invention because of the pivotal role they play in the induction of immune responses to antigens; they can both process as well as present antigens to cellular elements of the immune system and are able to prime naive CTL. Dendritic cells can be obtained from bone marrow according to the methods of Mayordomo et al. *Nature Medicine* 1:1297–1302 (1995), or by any other means known in the art.

For the methods of the present invention, APCs should first be generated by any suitable means known in the art. Peptides comprising the T-cell defined epitopes should then be pulsed onto the APC by incubating a suspension of APC with the peptide at 37° C. for about 1 hour. These epitopes are peptides of gp110 characterized as being naturally processed and presented on the cell surface in association with MHC Class I or Class II molecules for T-cell recognition. Any other means known in the art for peptide pulsing can also be employed. A vaccine is thereby created in the form of the APC containing the peptide fragment. The APC vaccine is then administered to a host. The vaccine can be administered to a patient by parenteral injection, such as intravenously, intrathecally, intramuscularly or intraarterially, or by subcutaneous injection. The vaccine can be administered through the use of any suitable pharmaceutical carrier or adjuvant, such as physiological salt solution.

Alternatively, bioballistic injection can be used to directly introduce into a host a substantially pure gp110 cDNA encoding an antigenic fragment. This injection can be accomplished, for example, by use of a microprojectile bombardment device. This device injects particles into a host, such as gold beads, which are coated with the gp110 cDNA. The particles coated with the cDNA are referred to as particulate polynucleotides. The cDNA is introduced to APCs in the host.

A further embodiment of this invention provides therapeutic treatment of a cancer patient which generally comprises administering to the patient an effective amount of a formulation comprising a substantially pure polypeptide fragment comprising an amino-terminal portion of glycoprotein 110, which has tumor rejection inducing activity. Preferably, this method employs the polypeptide fragment from amino acid 1 to amino acid 938. The method may also employ conservatively modified variants of this fragment. As with the prophylactic method, the method of administration preferably comprises incubating the protein fragment with APC, preferably autologous dendritic cells, and administering the APC to the patient. Bioballistic injection as described above can also be used.

As used herein, "effective amount" refers to that amount of a formulation comprising a substantially pure polypeptide fragment comprising gp110 necessary to impart the desired level of prophylactic or therapeutic treatment to a patient. As will be appreciated by those skilled in the art, the amount that will be effective will vary from patient to patient depending on such factors as the severity of the illness, if the methods are being used therapeutically, and the likelihood of getting the illness, if the methods are being used prophylactically. Determination of the effective amount for each patient is within the ordinary skill in the art, but will typically be about 100 μg of peptide per injection, with between about 4–6 injections being administered, with an injection given every one to two weeks. If using APCs pulsed with the peptide, a dosage of between about 2 and 20 million cells would typically be administered per patient.

The present invention is further directed to a pharmaceutical composition for treating cancer, either prophylactically or therapeutically, comprising a substantially pure polypeptide fragment of glycoprotein 110 in a suitable pharmaceutical carrier or adjuvant. Any suitable pharmaceutical carrier or adjuvant can be used, so long as compatibility problems do not arise, including but not limited to saline and dextrose injection. These pharmaceutical compositions may be administered to a patient by parenteral injection such as intravenously, intrathecally, intramuscularly or intraarterially.

The present invention is further directed to an animal model for the studying of tumors expressing elevated levels and/or conservatively modified forms of gp110, and evaluating the efficacy of gp110-based vaccines. Substantially pure polypeptide fragments of glycoprotein 110 prepared by recombinant DNA or synthetic methods, or cDNA encoding wild-type or conservatively altered amino acid gp110 sequences expressed in certain tumors, will be administered to naive mice either in the form of vaccines comprised of the immunogen and cellular or chemical adjuvants or by bioballistic injection in order to induce prophylactic resistance in these mice to these tumors. Cellular adjuvants include, but are not limited to, APCs such as dendritic cells and B cells; chemical adjuvants include, but are not limited to, commercially available adjuvants such as Incomplete Freunds Adjuvant and QS21. These methods are generally described in Examples 3–5. In a similar manner, the efficacy of the above-mentioned immunogens to induce tumor rejection in tumor-bearing mice can be determined. The results of these experiments define the efficacy of gp110-based vaccines.

The present invention is also directed to a method for studying the role of gp110 in human cancer. The polymorphism of human gp110, expression of conservatively altered gp110 sequences, and levels of expression of gp110 in tumors is determined through methods such as those described in the examples. Panels of tissues and cells obtained from normal individuals and tumor tissue and surrounding normal tissues obtained from cancer patients can be analyzed to determine polymorphism and alterations in gp110 transcripts using methods known to those skilled in the art, such as RT-PCR and its modifications.

The immunogenicity of substantially pure protein fragments of glycoprotein 110 prepared by recombinant DNA or synthetic methods, or cDNA encoding wild-type or conservatively altered amino acid gp110 sequences expressed in certain tumors, for use in human gp110 cancer vaccines can be evaluated by in vitro immunological assays, which are well known to those skilled in the art. The gp110-related agents will be used to induce anti-gp110 CTL from peripheral blood lymphocytes (PBL) of normal individuals and the anti-tumor reactivity of these CTL defined. Class I and Class II-associated gp110-derived epitopes capable of being recognized by T-cells can be identified according to these methods. The presence of anti-gp110 lymphocytes in PBL from cancer patients can also be studied using these methods.

In addition, anti-gp110 humoral immune responses of cancer patients is evaluated using highly purified human gp110 isolated from normal tissues or prepared by recombinant DNA methods. The sera of normal individuals, patients with non-cancerous diseases, and cancer patients can then be screened for anti-gp110 antibodies by a method such as Western Blot Analysis or ELISA. The specificity and frequency of occurrences of anti-gp110 antibodies in the sera of cancer patients is evaluated in comparison to a similar analysis of sera obtained from normal individuals and patients with non-neoplastic disorders. Frequency and titer of antibodies of gp110 will be much greater than those of normal individuals. Thus, the present invention functions as a serum tumor marker in the diagnosis and treatment of certain cancers.

The term "patient" as used herein includes members of the animal kingdom including but not limited to human beings.

EXAMPLES

The following examples are intended to illustrate the invention and should not be construed as limiting the invention in any way.

Example 1

Generation of Bone Marrow-Derived Dendritic Cells

Bone marrow (BM) cells, approximately $60 \times 10^6$ per mouse, were isolated from mice. Both BALB/c and C57BL/6 mice, obtained from The Jackson Laboratory, Bar Harbor, Me., were used. The isolated BM cells were immunodepleted of mature T and B cells by incubation of the BM cells with a cocktail of mAb (anti-CD4, anti-CD8, and anti-B220) and rabbit serum as the source of complement in a ratio of 1 to 8. This treatment reduced the number of BM cells by half. The cells were incubated overnight at 37° C. Following the incubation, the non-adherent cells (approximate yield $10 \times 10^6$ cells) were harvested and cultured in the presence of about 1,000 I.U./ml of GM-CSF and rIL-4 at a density of about $2.5 \times 10^5$ cells/ml complete medium/well in 24-well plates for 8 days. The addition of IL-4 to the cultures decreases the generation of granulocytes in the cultures. The cells were then harvested with an approximate yield of $6 \times 10^6$ cells. Flow cytometry analysis was then performed on the cells; the results indicated that the cells were approximately 60–70% B7+, CD45+, Ia+ and Mac1+, suggesting that approximately 60% of the cells are dendritic cells (DC).

Example 2

Functional Characterization of BM-Derived DC

The BM-Derived DC generated according to the method of Example 1 were found to be approximately 30 times more effective than normal splenocytes in eliciting an allogenic mixed lymphocyte reaction (MLR). Example 2 utilized splenocytes from B6 and BALC/c strains of mice. The results are shown in Table 1, and are based on the increased level of proliferation induced times the reciprocal of the number of cells required to induce 50% maximal stimulation.

TABLE 1

BM-derived DC are potent stimulator of the allogeneic mixed lymphocyte reaction (MLR).

| Stimulator cells | Maximum cpm $\times 10^{-3}$ | Number of stimulators needed for 50% maximum cpm |
|---|---|---|
| B6 DC | 97.4 +/− 4.0 10x | 1,000 |
| B6 splenocytes | 9.8 +/− 2.0 | 30,000 |
| BALB/c splenocytes | 2.4 +/− 0.5 | 30,000 |

Note: Responder cells were BALB/c splenocytes ($3 \times 10^5$/well).

Example 3

Immunization of Mice with DC-Based Vaccines

The efficacy of BM-derived DC-based vaccines was studied in two well-characterized tumor models—ovalbumin (OVA) and human papilloma virus type 16 (HPV16) E protein. Both of these tumor models involve CTL-defined H-2 associated peptides derived from proteins of xenogeneic origin.

Ovalbumin-transfected MO5 Murine Tumor Model

The efficacy of BM-derived DC and skin-derived Langerhans cells (LC) was compared. BM-derived DC were prepared as described in Example 1, and LC were prepared from a suspension of single cells derived from the epidermal layer of the skin. Both cell populations were pulsed with an ovalbumin-derived H-$2D^b$-binding peptide, $OVA_{245-253}$. $2.5 \times 10^6$ DC were incubated with about $10 \mu M$ of ovalbumin peptide for 2 hours on ice, washed, irradiated and injected intravenously into groups of mice in a concentration of about $10^5$ cells/mouse. The immunization was repeated 1 week later, and the mice were challenged 7 days following the second immunization with ovalbumin-transfected murine melanoma MO5 in a concentration of $5 \times 10^5$ cells. As can be seen from Table 2 and FIG. 2, the BM-derived DC-based vaccine (represented by the "+" symbols) were more effective than the LC-based vaccine represented by the "○" symbols in inducing tumor resistance as well as anti-OVA CTL in mice. The positive control for the CTL induction experiment shown in FIG. 2 was a vaccine consisting of splenocytes pulsed with the ovalbumin protein (represented by the "▲" symbols).

HPV16 E7 Peptide C3 Tumor Model

Mice were immunized with the HVP16 E7 49-57 peptide admixed with Incomplete Freund's Adjuvant (IFA) and Fetal Bovine Serum (FBS) in the same manner as described above. Following immunization, the mice were challenged with C3 cells in a concentration of $5 \times 10^5$. Immunization of mice with the E7 49-57 peptide admixed with IFA and FBS was shown to induce anti-peptide CTL and heightened the resistance of the mice to the lethal challenge by the C3 cells. It was also determined that the BM-derived DC cells pulsed with the E7 49-57 peptide were also highly efficient in increasing the resistance of mice to C3 cells. The vaccine consisting of IFA admixed with E7 49-57 peptide in the absence of FBS was found to be non-immunogenic. It is possible, therefore, that the FBS acts as a non-specific T helper component. The results are shown in Table 2.

TABLE 2

Immunization with antigen-pulsed BM-derived DC

| Immunization | Tumor Incidence[a] (day 21) | Mean Tumor Area (+/− SD) (day 21) |
|---|---|---|
| Ovalbumin (OVA 245-253)-peptide MO5 tumor model | | |
| DC + OVA peptide | 0/5 | 0(+/−0)[b] |
| LC + OVA peptide | 4/5 | 37.2 (+/−3.9) |
| Control | 5/5 | 46.7 (+/−5.2) |
| HPV16 E + L E7$_{49-57}$ peptide C3 tumor model | | |
| DC + E7$_{49-57}$ | 0/5 | 0(+/−0) |
| DC alone | 5/5 | 81.2 (+/−30.4) |
| IFA + E7$_{49-57}$/FBS− | 4/5 | 53.6 (+/−45.1) |
| IFA + E7$_{49-57}$/FBS+ | 1/5 | 15.8(+/−35.4 |
| IFA alone | 5/5 | 76.5 (+/−34.8) |
| Control | 5/5 | 66.8 (+/−21.8) |

[a]Number of mice with tumors/total tumors. Mice challenged with Meth A, OVA-M05 melanoma or HPV16-transfected C3 cells.
[b]Underlined values indicate significance of at least p < 0.05.

This example demonstrates the reliability of the methods used to test the gp110 vaccines of the present invention.

Example 4

Immunization of Mice with DC-based Meth A Vaccines

The efficacy of BM-derived DC-based vaccines was studied using a variety of immunogens, including Meth A gp110, Class I MHC-associated peptides derived from Meth A sarcoma, previously shown to contain CTL-defined epitopes (see Fassanito et al., Cancer Res. 55:124–128 (1995)) and wild type and mutated sequence peptides derived from the murine tumor suppressor gene product (p53). (See Mayordomo et al. J. Exp. Med. 183:1357–1365 (1996) for results using the wild-type p53 and mutated p53 product).
The Meth A Tumor Model For these experiments, a highly purified preparation of gp110 isolated from cell-free extracts of Meth A sarcoma by ion-exchange chromatography (Meth A gp110) and a fraction of Class I MHC associated peptides obtained from Meth A sarcoma and separated by HPLC (Fr27) were used as immunogens. Approximately 2.5–10$^5$ BM-derived DC per well were incubated either overnight at 37° C. with Meth A gp110 at concentrations of either 10 or 1 microgram per milliliter, 100 microliters of Fr27 (8–10$^7$ cells equivalents) for about 2 hours at 4° C., or a non-immunogenic dose of intact Meth A or CMS4 sarcoma in a concentration of 3×10$^4$. Following the incubation, the cells were harvested, washed and irradiated (10,000 rad). The Meth A sarcoma, Meth A gp110 or Meth A peptide Fr27 vaccines were then injected intravenously into three groups of BALB/c mice (10$^5$ cells per mouse), respectively. The immunization was repeated 8 days later. Ten days later, groups of 3 mice each were challenged subcutaneously with 2×10$^5$ Meth A sarcoma. Mice immunized with DC-based/Meth A sarcoma vaccines were completely protected from tumor growth. Immunization of mice with vaccines consisting of DC pulsed with Meth A gp110 or Meth A peptide Fr27 was less effective than the DC Meth A vaccine, but they still induced significant resistance to growth of Meth A sarcoma. Untreated mice and mice treated with 3×10$^4$ Meth A, DC alone or DC pulsed with CMS4 showed no resistance to tumor growth. In addition, the results indicated that the efficacy of gp110 pulsed vaccines was dose-dependent. The results are presented in Table 3.

TABLE 3

Immunization with antigen-pulsed BM-derived DC
Meth A tumor model

| Immunization | Tumor Incidence[a] (day 21) | Mean Tumor Area (+/−SD) (day 21) |
|---|---|---|
| DC + Meth A 3 × 10$^4$ | 0/5 | 0(+/−0) |
| DC + CMS4 3 × 10$^4$ | 5/5 | 61.2 (+/−5.3) |
| DC alone | 5/5 | 52.7 (+/−4.4) |
| Meth A 3 × 10$^4$ | 5/5 | 50.2 (+/−6.1) |
| Control | 5/5 | 51.3 (+/−3.7) |
| DC + Meth A gp110/10 μg | 1/3 | 21.0(+/−36.3) |
| DC + Meth A gp110/1 μg | 2/3 | 79.0 (+/−35.9) |
| DC alone | 3/3 | 96.4 (+/−21.8) |
| Control | 3/3 | 99.3 (+/−17.9) |
| DC + Meth A Fr27 | 4/5 | 69.5(+/−46.5) |
| DC + CS peptide | 5/5 | 151.6 (+/−48.8) |
| DC alone | 5/5 | 153.3 (+/−27.6) |
| Control | 5/5 | 138.1 (+/−18.7) |

[a]Number of mice with tumors/total tumors. Mice challenged with Meth A.
[b]Underlined values indicate significance of at least p < 0.05.

Example 5

Immunotherapy of C3-Bearing Mice with HPV16 E7-Pulsed DC Vaccine

Figure 3:
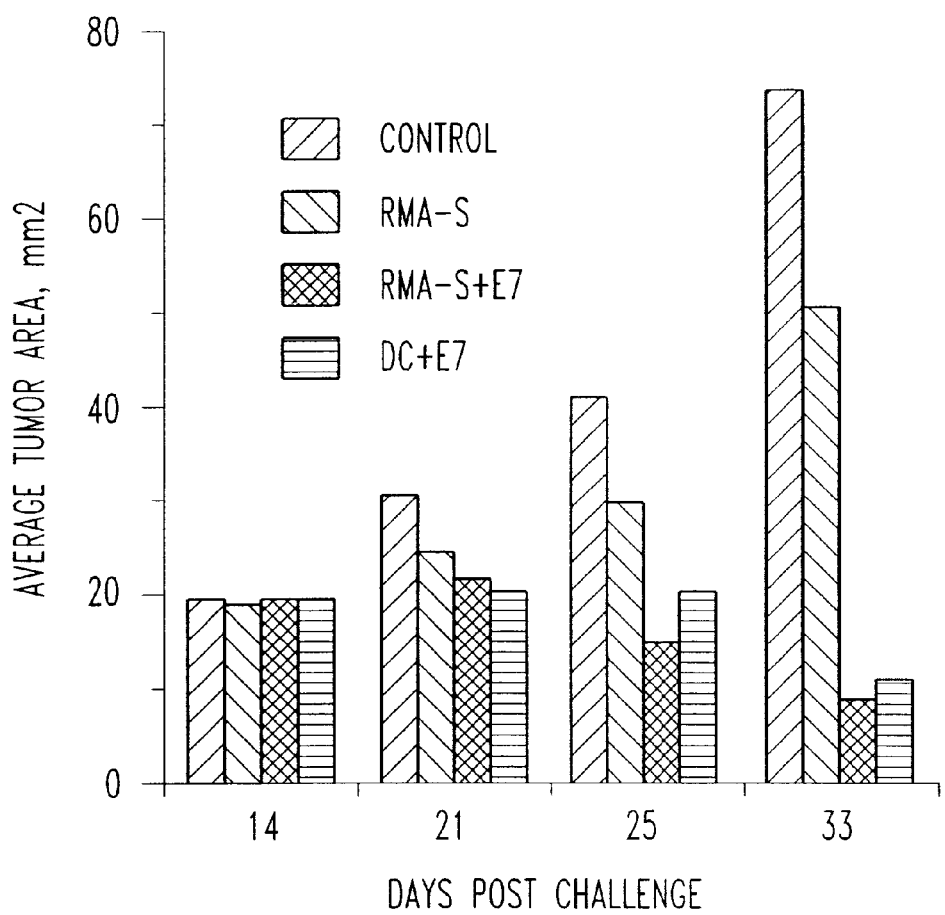
FIG. 3 shows the immunotherapeutic effect on established C3 tumors (day 14) with APC pulsed with HPV16 E7$_{49-57}$ peptide determined according to the methods of Example 5.

Locally growing C3 tumors were induced in mice by subcutaneous injection of about 5×10$^5$ in vitro grown C3 cells. After 14 days, the mice were given an immunotherapeutic dose (10$^5$) of DC-E7 peptide vaccine. The DC-based vaccine was compared to RMA-S tumor cells pulsed with the E7 peptide. Controls included untreated and RMA-S treated mice. As illustrated in FIG. 3, the peptide pulsed DC vaccine was about as effective as the RMA-S based vaccine in enhancing the resistance of the mice to progressive growth of the C3 tumor. The RMAs and control mice had tumors that were much larger in size. Although an unpulsed DC control was not included in this experiment, immunization of mice with unpulsed RMA-S had no effect, which negates an adjuvant effect for FBS in this system.

Example 6 gp110 in Human Tumors

Figure 4:
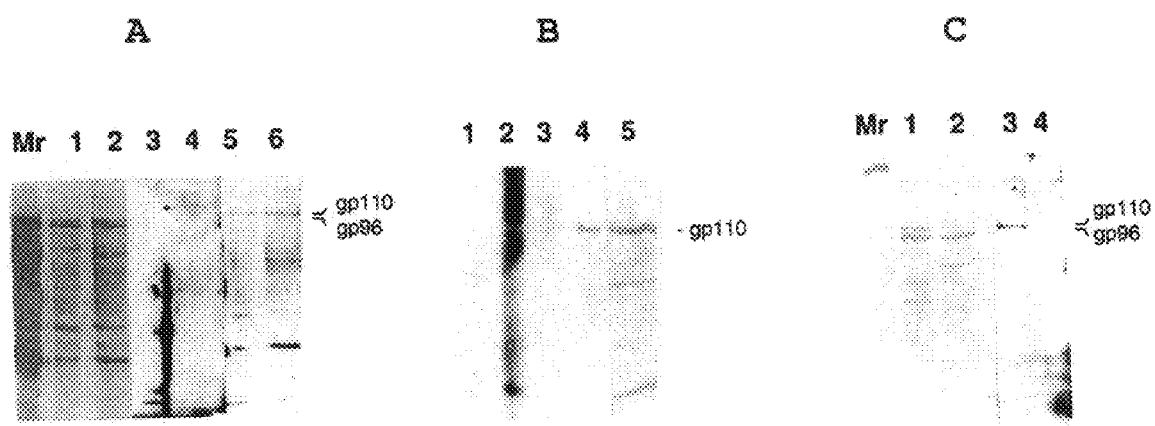
FIG. 4 shows the gp110 expression in BT-20 human breast cancer, as determined according to the methods of Example 6.
Figure 5:
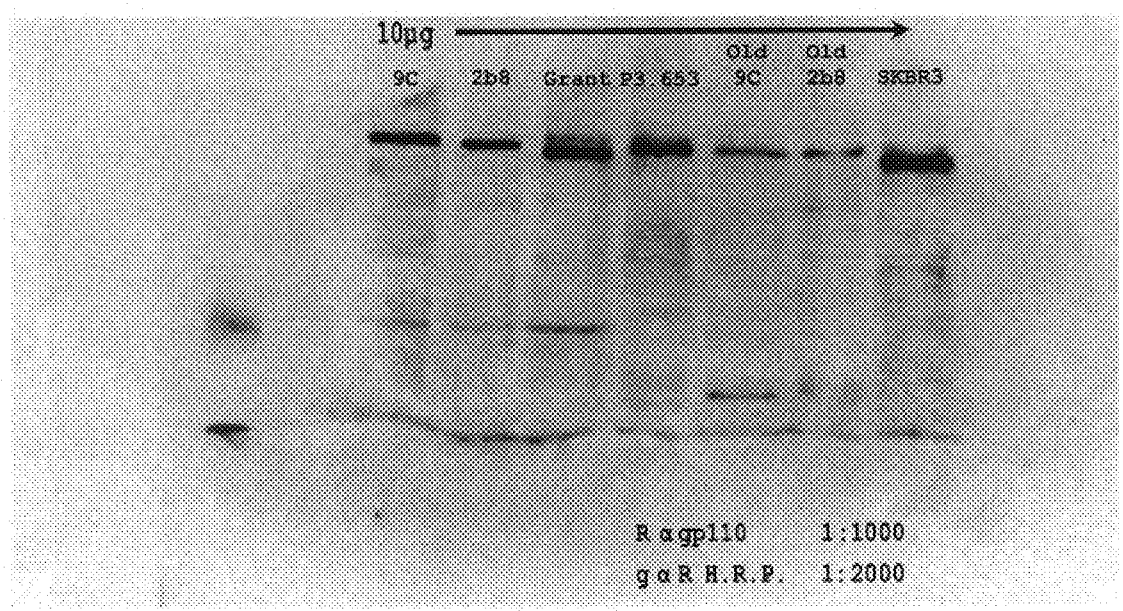
FIG. 5 illustrates that human gp110 was detected in SKBR3 breast carcinoma and a human melanoma, as determined according to the methods of Example 6.

An anti-Meth A gp110 monoclonal antibody (mAb) of rat origin and a rabbit anti-gp110 N-terminal peptide serum were used to detect the expression of gp110 in the Con A Sepharose-bound protein fraction of the human breast carcinoma cell line, BT-20, by immunoblot analyses. Results using the mAb as a probe are illustrated in FIG. 4A. Human gp110 was also detected in another breast carcinoma (SKBR3) as well as a human melanoma (FIG. 5). It was also determined by immunoblast analysis of ConA Sepharose bound protein fraction of BT-20 that IgG present in the sera of some breast cancer patients recognized an M$_r$ 110,000 species of gp110 present in this protein fraction. This is illustrated in FIG. 4B. These antibodies recognize human 110kDa protein but not murine gp110, as illustrated in FIG. 4C.

These findings show that gp110 is a common TRA for mouse and human tumors. The translational value of murine studies for humans is significant since epitopes recognized by the anti-tumor CTL, (Frassanito et al. 1995) as well as from the tumor models described in Examples 3 and 4 above show that gp110 has tumor rejection-inducing activity. Immunoblot analysis of normal and tumor cells of mouse and human origin indicate that in both species expression of gp110 is enhanced (3–5×) in transformed cells.

Example 7

Isolation and Sequencing of a cDNA Encoding gp110

Initially, Meth A gp110 was purified to homogeneity and digested with lysyl endoproteinase C; resulting peptides were fractionated by HPLC and selected fractions sequenced by automated Edman degradation. The following peptide sequences were obtained:

Fraction 9 (amino acids 216–226 of SEQ ID NO:1):
　Lys Asp Glu Pro Gly Ala Trp Glu Glu Thr Phe Lys
Fraction 28 (amino acids 875–902 of SEQ ID NO:1):
　Gly His Leu Glu Thr Pro Ile Trp Ile Glu Arg Val
　Val Ile Met Gly Ala Gly Lys Pro Ala Ala Val
　Val Leu Gln Thr Lys
Fraction 39 (amino acids 487–495 of SEQ ID NO:1):
　Thr Arg Asp Gly Ser Asp Tyr Glu Gly
Fraction 44 (amino acids 266–294 of SEQ ID NO:1):
　Thr Glu Gly Gly Glu Pro Tyr Arg Leu Tyr Asn
　Leu Asp Val Phe Gln Tyr Glu Leu Asn Asn Pro Met
　Ala Leu Tyr Gly Ser Val
Fraction 45 (amino acids 623–638 of SEQ ID NO:1):
　Ile Ser Ile Pro Met Cys Leu Ser Leu Ala Leu
　Val Gly Leu Ser Phe
These fractions are further identified in FIG. 1.

Degenerate oligonucleotide primers based on portions of peptide fraction 44 above were made and used in RT-PCR of mRNA isolated from cultured Meth A cells. A product of the expected size was cloned and sequenced, and allowed identification of the exact coding sequence for the portion of peptide 44 lying between the flanking PCR primers.

A reverse PCR primer was made corresponding to this exact coding sequence, and name Ir, for "Internal peptide, reverse". The Ir primer was used in combination with degenerate forward primers based on a portion of the N-terminal peptide sequence to perform additional RT-PCR on Meth-A mRNA. A fragment of 762 bp in length was recovered, encoding 254 amino acids. Within the deduced amino acid sequence of this fragment a sequence corresponding to peptide fraction 9 was identified, confirming that the fragment encoded for the same protein species isolated by biochemical means.

A phage library incorporating cDNA from Meth A mRNA was made at the NCI; however, screening of this library by PCR using primers designed to recover the 762 bp fragment failed to reveal the expected product. Additional libraries were screened for the presence of gp110 cDNA; one such library was derived from 18–1 cells, which are b-raf-transformed NIH 3T3 murine fibroblasts. This library was used for subsequent screening using standard protocols, and using the 762 bp PCR fragment as a probe.

Three rounds of phage library screening gave rise to a phage population (designated 10.2) that possessed a cDNA having the expected sequence. This phage population failed to propagate further. To overcome this problem, the phage lysate was subjected to PCR and a 3.8 kb fragment was isolated, which:
　contained coding sequence for the additional peptides identified by Edman sequencing,
　contained the entire 3' untranslated region of cDNA, including the polyA tail,
　contained sequence upstream (i.e., 5' to) the protein's presumptive amino terminus, but did not include the expected methionine start codon.

Results of sequencing are presented in FIG. 1.

Example 8

Determination of Heterogeneity in gp110 Amino Acid Sequence cDNA's encoding a specific region (amino acid 27 to amino acid 210) of gp110 were isolated from BALB/c thymus, spleen and fibroblasts, as well as the chemically induced Meth A and CMS4 sarcomas (tumors). These cDNA's were isolated by reverse transcription of two micrograms of RNA purified from each cell type, followed by polymerase chain reaction (PCR) amplification using oligonucleotides that flank nucleotide sequence of the specific region. The PCR products were then ligated into a plasmid vector, purified by standard techniques, and sequenced on both strands by the dideoxy chain termination method. Sequences were obtained from two different preparations each of BALB/c thymus, spleen and one of fibroblasts. The nucleotide sequences were translated to amino acid sequences, and their examination demonstrated that the sequences were greater than 90% homologous to each other and to the original gp110 sequence. However, specific differences in amino acids were identified which indicate polymorphism in sequences, gp110 transcripts expressed in normal tissues and, possibly, missense mutations in gp110 transcripts sequences expressed in tumor cells (FIG. 6).

FIG. 6 shows the polymorphic characteristics of gp110 taken from several different sources. As used in the figure, RT/PCR products identified as CMS4-1, Meth A-1 and CMS4-2 were generated from mRNA obtained from tumors and alpha-1, alpha-2, alpha-3, beta-1 and beta-2 were obtained in a similar manner from mRNA obtained from normal tissues. Alpha-1 and alpha-3 were obtained from spleen, alpha-2 from spleen and fibroblasts, beta-1 from thymus and beta-2 from thymus and fibroblasts. As can be seen from the figure, there are numerous points of diversity among the sequences of the RT/PCR products generated from the various sources, yet all of these sequences encode gp110. This confirms the polymorphic characteristics of gp110.

Whereas particular embodiments of this invention have been described above for purposes of illustration, it will be evident to those skilled in the art that numerous variations of the details of the present invention may be made without departing from the invention as defined in the appended claims.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 938 amino acids
      (B) TYPE: amino acid
      (D) TOPOLOGY: linear (ii) MOLECULE TYPE:

(iii) HYPOTHETICAL: NO (iv) ANTI-SENSE: NO (v) FRAGMENT TYPE: N-terminal (vi) ORIGINAL SOURCE:
      (A) ORGANISM: Mus musculus
      (D) DEVELOPMENTAL STAGE: Embryo
      (F) TISSUE TYPE: Embryo
      (H) CELL LINE: NIH 3T3

(xi) SEQUENCE DESCRIPTION: SEQ ID NO:1:

```
Ala Ala Val Ala Ala Arg Arg Arg Ser Trp Leu Ser Leu Val Leu
 1               5                  10                  15

Ala Tyr Leu Gly Val Cys Leu Gly Ile Thr Leu Ala Val Asp Arg Ser
            20                  25                  30

Asn Phe Lys Thr Cys Asp Glu Ser Ser Phe Cys Lys Arg Gln Arg Thr
            35                  40                  45

Ile Arg Pro Gly Leu Ser Pro Tyr Pro Ser Leu Leu Asp Thr Leu Gln
 50                  55                  60

Leu Gly Pro Asp Ala Leu Thr Val His Leu Ile His Glu Val Thr Lys
 65                  70                  75                  80

Val Leu Leu Val Leu Glu Leu Gln Gly Leu Gln Lys Asn Met Thr Arg
                85                  90                  95

Ile Arg Ile Asp Glu Leu Glu Pro Arg Pro Arg Tyr Arg Val Pro Asp
            100                 105                 110

Val Leu Val Ala Asp Pro Pro Thr Ala Arg Leu Ser Val Ser Gly Arg
            115                 120                 125

Asp Asp Asn Ser Val Glu Leu Thr Val Ala Glu Gly Pro Tyr Lys Ile
            130                 135                 140

Ile Leu Thr Ala Gln Pro Phe Arg Leu Asp Leu Leu Glu Asp Arg Ser
145                 150                 155                 160

Leu Leu Leu Ser Val Asn Ala Arg Gly Leu Met Ala Phe Glu His Gln
                165                 170                 175

Arg Ala Pro Arg Val Pro Gln Glu Ser Lys Asp Pro Ala Glu Gly Asn
            180                 185                 190

Gly Ala Gln Pro Glu Ala Thr Pro Gly Asp Gly Asp Lys Pro Glu Glu
            195                 200                 205

Thr Gln Glu Lys Ala Glu Lys Asp Glu Pro Gly Ala Trp Glu Glu Thr
            210                 215                 220

Phe Lys Thr His Ser Asp Ser Lys Pro Tyr Gly Pro Thr Ser Val Gly
225                 230                 235                 240

Leu Asp Phe Ser Leu Pro Gly Met Glu His Val Tyr Gly Ile Pro Glu
                245                 250                 255
```

-continued

His Ala Asp Ser Leu Arg Leu Lys Val Thr Glu Gly Gly Glu Pro Tyr
            260                 265                 270

Arg Leu Tyr Asn Leu Asp Val Phe Gln Tyr Glu Leu Asn Asn Pro Met
            275                 280                 285

Ala Leu Tyr Gly Ser Val Pro Val Leu Leu Ala His Ser Phe His Arg
            290                 295                 300

Asp Leu Gly Ile Phe Trp Leu Asn Ala Ala Glu Thr Trp Val Asp Ile
305                 310                 315                 320

Ser Ser Asn Thr Ala Gly Lys Thr Leu Phe Gly Lys Met Leu Asp Tyr
                    325                 330                 335

Leu Gln Gly Ser Gly Glu Thr Pro Gln Thr Asp Ile Arg Trp Met Ser
                    340                 345                 350

Glu Ser Gly Ile Ile Asp Val Phe Leu Met Leu Gly Pro Ser Val Phe
                    355                 360                 365

Asp Val Phe Arg Gln Tyr Ala Ser Leu Thr Gly Thr Gln Ala Leu Pro
            370                 375                 380

Pro Leu Phe Ser Leu Gly Tyr His Gln Ser Arg Trp Asn Tyr Arg Asp
385                 390                 395                 400

Glu Ala Asp Val Leu Glu Val Asp Gln Gly Phe Asp Asp His Asn Met
                    405                 410                 415

Pro Cys Asp Val Ile Trp Leu Asp Ile Glu His Ala Asp Gly Lys Arg
                    420                 425                 430

Tyr Phe Thr Trp Thr Pro Thr Arg Phe Pro Gln Pro Leu Asn Met Leu
            435                 440                 445

Glu His Leu Asp Ser Lys Arg Arg Asn Val Val Ala Ile Val Asp Pro
450                 455                 460

His Ile Lys Val Asp Ser Gly Tyr Arg Val His Glu Glu Leu Arg Asn
465                 470                 475                 480

His Gly Leu Tyr Val Lys Thr Arg Asp Gly Ser Asp Tyr Glu Gly Trp
                    485                 490                 495

Cys Trp Pro Gly Ser Ala Ser Tyr Pro Asp Phe Thr Asn Pro Arg Met
                    500                 505                 510

Arg Ala Leu Trp Ser Asn Met Phe Ser Phe Asp Asn Tyr Glu Gly Ser
            515                 520                 525

Ala Pro Asn Leu Tyr Val Trp Asn Asp Met Asn Glu Pro Ser Val Phe
            530                 535                 540

Asn Gly Pro Glu Val Thr Met Leu Lys Asp Ala Val His Tyr Gly Gly
545                 550                 555                 560

Trp Glu His Arg Asp Ile His Asn Ile Tyr Gly Leu Tyr Val His Met
                    565                 570                 575

Ala Thr Ala Asp Gly Leu Ile Gln Arg Ser Gly Gly Ile Glu Arg Pro
                    580                 585                 590

Phe Val Leu Ser Arg Ala Phe Phe Ser Gly Ser Gln Arg Phe Gly Ala
            595                 600                 605

Val Trp Thr Gly Asp Asn Thr Ala Glu Trp Asp His Leu Lys Ile Ser
            610                 615                 620

Ile Pro Met Cys Leu Ser Leu Ala Leu Val Gly Leu Ser Phe Cys Gly
625                 630                 635                 640

Ala Asp Val Gly Gly Phe Phe Lys Asn Pro Glu Pro Glu Leu Leu Val
                    645                 650                 655

Arg Trp Tyr Gln Met Gly Ala Tyr Gly Pro Phe Phe Arg Ala His Ala
                    660                 665                 670

Thr Trp Thr Leu Gly Gly Glu Ser Met Ala Val Ser Val Ser Ile Pro

```
                    675                 680                 685

Arg Cys Asn Pro Arg Cys Leu Val Pro Ala Ile Phe Phe Ala Ala Leu
            690                 695                 700

Leu Val Tyr Pro Leu Leu Ser Ser Ser Gln Gly Arg Val Ser Cys His
705                 710                 715                 720

Glu Ala Pro Leu Val Gln Tyr Pro Glu Asp Met Ser Thr Phe Ser Ile
                725                 730                 735

Glu Asp Gln Phe Met Leu Gly Asp Ala Leu Leu Ile His Pro Val Ser
            740                 745                 750

Asp Ala Gly Ala His Gly Gly Arg Ser Ile Cys Leu Ala Lys Lys Arg
            755                 760                 765

Cys Gly Met Thr Phe Arg Ala Ile Arg Ser Ile Met Gly Pro Arg Pro
770                 775                 780

Cys Ile Cys Pro Val Thr Leu Ser Ser Ile Pro Val Phe Gln Gly Gly
785                 790                 795                 800

Gly Thr Ile Val Pro Arg Trp Met Arg Val Arg Ser Ser Asp Cys
            805                 810                 815

Met Lys Asp Asp Pro Ile Thr Leu Phe Val Ala Leu Ser Pro Gln Gly
            820                 825                 830

Thr Ala Gln Gly Glu Leu Phe Leu Asp Asp Gly His Thr Phe Asn Tyr
            835                 840                 845

Gln Thr Arg His Glu Phe Leu Leu Arg Arg Phe Ser Phe Ser Gly Ser
850                 855                 860

Thr Leu Val Ser Ser Ser Ala Asp Pro Lys Gly His Leu Glu Thr Pro
865                 870                 875                 880

Ile Trp Ile Glu Arg Val Val Ile Met Gly Ala Gly Lys Pro Ala Ala
                885                 890                 895

Val Val Leu Gln Thr Lys Gly Ser Pro Glu Ser Arg Leu Ser Phe Gln
            900                 905                 910

His Asp Pro Glu Thr Ser Val Leu Ile Leu Arg Lys Pro Gly Val Ser
            915                 920                 925

Val Ala Ser Asp Trp Ser Ile His Leu Arg
930                 935

(2) INFORMATION FOR SEQ ID NO:2:

(i) SEQUENCE CHARACTERISTICS:
        (A) LENGTH: 50
        (B) TYPE: amino acid
        (C) TOPOLOGY: linear (ii) MOLECULE TYPE:

(xi) SEQUENCE DESCRIPTION:SEQ ID NO:2:

Pro Lys Glu Leu Val Leu Ser Trp Glu Glu Gly His Asp Gly Ile Glu
1               5                   10                  15

Leu Pro Phe Leu Leu Pro Trp Ser Leu Thr Leu Pro Arg Phe His Leu
            20                  25                  30

Leu Ile Leu Arg Pro Arg Phe Cys Gln His Leu Gly Lys Met Thr Gly
            35                  40                  45

Leu Ser
50

(2) INFORMATION FOR SEQ ID NO:3:

(i) SEQUENCE CHARACTERISTICS:
        (A) LENGTH: 6
```

```
          (B) TYPE: amino acid
          (C) TOPOLOGY: linear (ii) MOLECULE TYPE:

(xi) SEQUENCE DESCRIPTION:SEQ ID NO:3:

Gly Ser Glu Phe His Leu
1               5

(2) INFORMATION FOR SEQ ID NO:4:

(i) SEQUENCE CHARACTERISTICS:
          (A) LENGTH:  63
          (B) TYPE: amino acid
          (C) TOPOLOGY: linear (ii) MOLECULE TYPE:

(xi) SEQUENCE DESCRIPTION:SEQ ID NO:4:

Pro Ser Leu Ser Phe Cys Val Leu Pro Ser Pro Ser Tyr Ser Val Ser
1               5                   10                  15

Cys Cys Cys Asn Trp Ser Thr Val Ile Cys Glu His Gln Gly Ala Leu
            20                  25                  30

Ser Phe Phe Phe Ser Ser Leu Gly Ser Leu Pro Ser Pro Tyr Thr Pro
        35                  40                  45

Ser Ile Gln Ala Ser Cys Leu Leu Met Pro Phe Leu Gly Arg Arg
    50                  55                  60

(2) INFORMATION FOR SEQ ID NO:5:

(i) SEQUENCE CHARACTERISTICS:
          (A) LENGTH:  23
          (B) TYPE: amino acid
          (C) TOPOLOGY: linear (ii) MOLECULE TYPE:

(xi) SEQUENCE DESCRIPTION:SEQ ID NO:5:

Thr Leu Gly Phe Leu Phe Phe Phe Pro Val Pro Ser Tyr Pro Lys Cys
1               5                   10                  15

Pro Ser Phe His Ser Phe Pro
            20

(2) INFORMATION FOR SEQ ID NO:6:

(i) SEQUENCE CHARACTERISTICS:
          (A) LENGTH:  7
          (B) TYPE: amino acid
          (C) TOPOLOGY: linear (ii) MOLECULE TYPE:

(xi) SEQUENCE DESCRIPTION:SEQ ID NO:6:

Met Ser Pro Ser Leu Phe His
1               5

(2) INFORMATION FOR SEQ ID NO:7:

(i) SEQUENCE CHARACTERISTICS:
          (A) LENGTH:  44
          (B) TYPE: amino acid
          (C) TOPOLOGY: linear (ii) MOLECULE TYPE:

(xi) SEQUENCE DESCRIPTION:SEQ ID NO:7:
```

```
Tyr Thr Gly Thr Thr Pro Tyr Leu Val Arg Asp Lys Trp Ile Lys Ile
 1               5                  10                  15

Glu Val Pro Gly Glu Arg Pro Leu Pro Ser His Leu Asn Leu Val Phe
                20                  25                  30

Leu Phe Leu Ser Arg Ala Ala Ala Phe Leu Pro Ser
                35                  40
```

(2) INFORMATION FOR SEQ ID NO:8:

(i) SEQUENCE CHARACTERISTICS:
        (A) LENGTH: 7
        (B) TYPE: amino acid
        (C) TOPOLOGY: linear (ii) MOLECULE TYPE:

(xi) SEQUENCE DESCRIPTION:SEQ ID NO:8:

```
Arg Glu Thr Leu Pro His Asn
 1               5
```

(2) INFORMATION FOR SEQ ID NO:9:

(i) SEQUENCE CHARACTERISTICS:
        (A) LENGTH: 57
        (B) TYPE: amino acid
        (C) TOPOLOGY: linear (ii) MOLECULE TYPE:

(xi) SEQUENCE DESCRIPTION:SEQ ID NO:9:

```
Glu Gly Lys Val Ile Lys Leu Leu Pro Leu Trp Ser Pro Trp Asp
 1               5                  10                  15

Thr Gln Asp Arg Asp Met Ser Cys Gly Phe Thr Glu Ser Arg Ser Pro
                20                  25                  30

Val Phe Ile Ala Gly Lys Lys Thr Glu Gly Gly Arg Arg Ser Cys
                35                  40                  45

Val Pro Arg Gly Gly Phe Lys Pro Trp
    50                  55
```

(2) INFORMATION FOR SEQ ID NO:10:

(i) SEQUENCE CHARACTERISTICS:
        (A) LENGTH: 32
        (B) TYPE: amino acid
        (C) TOPOLOGY: linear (ii) MOLECULE TYPE:

(xi) SEQUENCE DESCRIPTION:SEQ ID NO:10:

```
Gly Arg Thr Gln Glu Pro Gly Glu Leu Phe Val Gly Ile Phe Phe Thr
 1               5                  10                  15

Ser Ser Gly Phe Pro Thr Val Thr Ser Phe Asp Lys Lys Glu Lys Gln
                20                  25                  30
```

(2) INFORMATION FOR SEQ ID NO:11:

(i) SEQUENCE CHARACTERISTICS:
        (A) LENGTH: 16
        (B) TYPE: amino acid
        (C) TOPOLOGY: linear (ii) MOLECULE TYPE:

(xi) SEQUENCE DESCRIPTION:SEQ ID NO:11:

```
Lys Thr Lys Gln Asn Ile Asn Asn Trp Met Ser Glu Leu Tyr Leu
```

-continued

```
1               5              10             15
```

(2) INFORMATION FOR SEQ ID NO:12:

(i) SEQUENCE CHARACTERISTICS:
        (A) LENGTH:  8
        (B) TYPE:   amino acid
        (C) TOPOLOGY:  linear (ii) MOLECULE TYPE:

(xi) SEQUENCE DESCRIPTION:SEQ ID NO:12:

```
Thr Glu Gln Asn Arg Ser Ser Lys
1               5
```

What is claimed is:

1. An isolated cDNA molecule consisting essentially of a polynucleotide sequence encoding a protein fragment of murine glycoprotein 110, wherein said polynucleotide sequence encodes the amino acid sequence of SEQ ID NO:1, or conservative variants thereof, said variants capable of inducing anti-gp 110 cytotoxic lymphocytes in the peripheral blood of normal individuals.

2. A cDNA vaccine for inducing resistance to tumors in a patient, wherein said cDNA encodes the amino acid sequence of SEQ ID NO:1, or conservative variants thereof, said variants capable of inducing anti-gp 110 cytotoxic lymphocytes in the peripheral blood of normal individuals.

3. An antigen presenting cell transfected with the cDNA vaccine of claim 2.

4. A method for providing tumor resistance response in a patient comprising vaccinating said patient with a prophylactically effective amount of a formulation comprising the cDNA molecule of claim 1.

5. The method of claim 4 further comprising the steps of transfecting the cDNA molecule into an antigen presenting cell and administering said cell to said patient.

6. The method of claim 5, wherein said antigen presenting cell is a dendritic cell.

7. The method of claim 4, further comprising the steps of distributing said cDNA molecule on a particle surface to form a particulate polynucleotide and inoculating said patient with said particulate polynucleotide.

* * * * *

UNITED STATES PATENT AND TRADEMARK OFFICE
CERTIFICATE OF CORRECTION

PATENT NO.    : 6,514,493 B1                                                Page 1 of 1
DATED         : February 4, 2003
INVENTOR(S)   : Albert B. DeLeo et al.

It is certified that error appears in the above-identified patent and that said Letters Patent is hereby corrected as shown below:

<u>Column 1,</u>
Line 5, "This work was supported, in part, by National Institute of Health grant CA42276.", should read -- This work was supported, in part, by National Institute of Health grant CA44276 --.
Line 36, "detect" should read -- detectable --.

<u>Column 3,</u>
Line 40, "SEQ ID NO: 1", should read -- "SEQ ID NO. 1, --.

<u>Column 8,</u>
Line 45, " " " " ", should read -- "0" --.

<u>Column 23,</u>
Line 25, "inducting" should read -- inducing --.

Signed and Sealed this

Sixteenth Day of September, 2003

JAMES E. ROGAN
*Director of the United States Patent and Trademark Office*